(12) United States Patent
Hölderich et al.

(10) Patent No.: US 6,531,595 B2
(45) Date of Patent: Mar. 11, 2003

(54) METHOD FOR PRODUCING ε-CAPROLACTAM AND REACTOR FOR THE METHOD

(75) Inventors: Wolfgang F. Hölderich, Frankenthal (DE); Gerd Dahlhoff, Bergheim (DE); Hiroshi Ichihashi, Otsu (JP); Keisuke Sugita, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/963,603

(22) Filed: Sep. 27, 2001

(65) Prior Publication Data

US 2002/0042509 A1 Apr. 11, 2002

(30) Foreign Application Priority Data

Sep. 29, 2000 (JP) .................................... 2000-300265

(51) Int. Cl.$^7$ ............................................. C07D 201/04
(52) U.S. Cl. ........................................................ 540/536
(58) Field of Search .......................................... 540/536

(56) References Cited

U.S. PATENT DOCUMENTS 6,071,844 A   6/2000   Hoelderich et al. ........... 502/77

FOREIGN PATENT DOCUMENTS

| DE | 19608660 A1 | 11/1996 |
| DE | 100 10 189 | * 9/2000 |
| EP | 1028108 A1 | 8/2000 |
| GB | 695 319 A | 8/1953 |

OTHER PUBLICATIONS

Albers et al., Journal of Castalysis, 176, 561–568 (1998).*
*Ullmann's Encyclopedia of Industrial Chemistry*, vol. B4, Part B, pp. 239–274.
Dahlhoff et al, American Chemical Society, Division of Enviromental Chemistry Reprints of Extended Abstracts, vol. 40 (1), pp. 177–179 Mar. (2000).
Takahashi et al, Stud. Surf. Sci. Catal, 97, pp. 431–436 (1995).

* cited by examiner

*Primary Examiner*—Bruck Kifle
(74) *Attorney, Agent, or Firm*—Birch, Stewart, Kolasch & Birch, LLP (57) ABSTRACT

A method is provided for producing ε-caprolactam from cyclohexanone oxime by using a zeolite or non-zeolitic material as a catalyst under gas phase reaction conditions. The method comprises a reaction step converting cyclohexanone oxime into ε-caprolactam in the presence of the zeolite or non-zeolitic material; and a regeneration step of treating the zeolite or non-zeolitic material with a non-oxidizing gas at a temperature of from about 100°C. to about 600° C.

8 Claims, 4 Drawing Sheets

METHOD FOR PRODUCING ε-CAPROLACTAM AND REACTOR FOR THE METHOD

FIELD OF THE INVENTION

The present invention relates to a method for producing ε-caprolactam from cyclohexanone oxime and, more specifically, a method for producing ε-caprolactam including the step of regenerating a zeolite or non-zeolitic material having lowered activity and a reactor for the method.

BACKGROUND OF THE INVENTION

ε-caprolactam is an important chemical raw material used as a basic material for the production of nylon and the like. In a classical method for producing ε-caprolactam, cyclohexanone oxime is rearranged to ε-caprolactam in liquid phase using concentrated sulfuric acid or fuming sulfuric acid as a catalyst (liquid phase Beckmann rearrangement reaction).

However, in the method using a liquid phase Beckmann rearrangement reaction, a large amount of ammonia is required for neutralizing the sulfuric acid, and consequently, a large amount of ammonium sulfate is produced as a by-product and significant costs arise due to the necessary treatment thereof.

Therefore, a method in which cyclohexanone oxime in the gas phase is Beckmann-rearranged using a solid catalyst (gas phase Beckmann rearrangement reaction) has been studied for a long time.

In the gas phase Beckmann rearrangement reaction, a cyclohexanone oxime vapor is reacted in the presence of a solid catalyst. The solid catalyst may be, for example, (1) a silica gel catalyst (U.S. Pat. No. 2,234,566), (2) a silica alumina catalyst (GB Patent No. 831,972), or (3) a zeolite catalyst (Journal of Catalysis, Vol. 6, p. 247, 1996, and U.S. Pat. Nos. 4,359,421 and 5,741,904).

Among them, crystalline zeolite catalysts having various compositions have been developed. This is because zeolite catalysts are known to have excellent catalyst life and selectivity to ε-caprolactam as compared with silica-based catalysts and the like.

In the gas phase Beckmann rearrangement reaction, deposits are generated on the surface of the catalyst during the reaction, and as a result, the activity of the catalyst is gradually lowered. In order to regenerate the deactivated catalyst, the catalyst is burned under an oxygen-containing gas at a high temperature.

In the case of burning the catalyst with oxygen, however, a significant heat release is caused by oxidation, whereby the temperature of catalyst rises. Furthermore, when deposits such as carbonaceous components (i.e. so-called coke) present on the catalyst are oxidized, water is produced which adversely influences the catalyst itself.

SUMMARY OF THE INVENTION

One object of the present invention is to provide a method for producing ε-caprolactam by a catalyst regeneration method capable of suppressing the deterioration of the catalyst.

This object and other objectives are achieved by the present invention which provides a method for producing ε-caprolactam from cyclohexanone oxime by using a zeolite or non-zeolitic material as a catalyst under gas phase reaction conditions. The method includes a reaction step for converting cyclohexanone oxime into E-caprolactam in the presence of the zeolite or non-zeolitic material, and a regeneration step of treating the zeolite or non-zeolitic material with a non-oxidizing gas at a temperature of from about 100° C. to about 600° C.

Also, the present invention provides a reactor charged with a zeolite or non-zeolitic material and having a reaction zone in which the zeolite or non-zeolitic material is utilized as a catalyst. A regeneration zone is also provided for the zeolite or non-zeolitic material, and a means for circulating the zeolite or non-zeolitic material between the reaction zone and the regeneration zone.

BRIEF DESCRIPTION OF THE DRAWINGS

FIGS. 2 (*a*), (*b*) and (*c*) are schematic diagrams of a U-valve, J-valve and L-valve, respectively, which may be utilized as a standpipe in FIG. 1.

DETAILED DESCRIPTION OF THE INVENTION

In the present invention, ε-caprolactam is produced from cyclohexanone oxime by using a zeolite or non-zeolitic material as a catalyst under gas phase reaction conditions. The method for producing ε-caprolactam comprises a reaction step for converting cyclohexanone oxime into ε-caprolactam in the presence of the zeolite or non-zeolitic material and a regeneration step of treating the zeolite or non-zeolitic material with a non-oxidizing gas at a temperature of from about 100° C. to about 600° C.

Examples of the zeolite suitable for use as a catalyst in the present invention include crystalline aluminosilicates, crystalline metallosilicates and the like. The crystalline metallosilicates may have a Si/M atomic ratio of about 5 or more, and preferably have a Si/M atomic ratio of about 50 or more, wherein M represents at least one element selected from the group consisting of B, Al, Ga, Fe, Ti and Zr. The Si/M atomic ratio can be measured by atomic absorption analysis, fluorescence X-ray analysis and the like.

Preferably, the crystalline zeolite is a so-called "high-silica" zeolite in which the main element consisting of a zeolite skeleton is substantially silicon, or a MFI zeolite containing boron as a main element in the zeolite skeleton (hereinafter, referred to as [B]-MFI zeolote).

Crystalline zeolite suitable for use in the present invention can be produced by known methods. For example, it can be produced by conducting a hydrothermal synthesis reaction of a mixture of a silica source, water and organic amine or quaternary ammonium compound (and further metal source or alkaline metal hydroxide added if necessary) in an autoclave, drying and calcining the resulting crystals, and if necessary, conducting ion exchange with an ammonium salt and the like, and drying again. Further, there are crystalline metallosilicates having various structures. It is preferred to use a crystalline metallosilicate having a pentasil-type structure such as MFI or MEL type.

For example, "Silicalite-1" which is a high-silica, MFI-type zeolite can be obtained by subjecting a mixture of tetraethylorthosilicate, water and tetrapropylammonium hydroxide (and further alkaline metal hydroxide added if necessary) to a hydrothermal synthesis under autogeneous pressure. A zeolite containing boron can be obtained by subjecting a mixture of silica, hexamethylenediamine and water to a hydrothermal synthesis under autogeneous pressure.

Examples of the non-zeolite material suitable for use as a catalyst in the present invention include phosphates, especially aluminophosphastes (AlPO) (as in European Patent No. 132,708 and U.S. Pat. Nos. 4,310,440 and 4,473,663), siliciumaluminophosphates (SAPO) (European Patent No. 103117 and U.S. Pat. No. 4,440,871), siliciumferrophosphates, cerophosphates, cironophosphates, boronphosphates, ferrophosphates and the like, as well as mixtures thereof.

The non-zeolitic material preferably is an aluminophosphates or siliciumaluminophosphates. The aluminophosphates such as AlPO-5, AlPO-11, AlPO-12, AlPO-14, AlPO-21, AlPO-25, AlPO-31, AlPO-33 can be hydrothermically produced as described in e.g. EP 132708.

For example, AlPO-5 can be obtained by mixing orthophosphoric acid with pseudoboehmite (Catapal SB™) in water, adding tetra-propylammoniumhydroxide thereto, stirring the resulting mixture at about 150° C. for 20–60 hours and filtering the mixture to obtain $AlPO_4$, followed by drying at 100–160° C. and calcining at 450–550° C.

The siliciumaluminophosphate can be obtained, for example, by mixing $SiO_2$ suspended in an aqueous tetra-propylammroniumhydroxide solution with an aqueous suspension of pseudoboehmite and orthophosphoric acid at 150–200° C. for 20–200 hours under autogeneous pressure in an autoclave to obtain a siliciumaluminophosphate powder, followed by drying at 110–160° C. and calcining at 450–550° C.

The zeolite and non-zeolitic material to be used is preferably in the form of powder or particles, and preferably have a particle size of from about 0.001 mm to about 5 mm, and more particularly have a particle size of from about 0.02 mm to about 3 mm.

In the present invention, a zeolite or non-zeolitic material is used as a catalyst in a gas phase Beckmann rearrangement reaction in which cyclohexanone oxime is rearranged to ε-caprolactam. The reaction may be conducted in a fixed-bed-type reactor or in a fluidized-bed-type reactor. In this reaction, a raw material, i.e., cyclohexanone oxime, is introduced in the form of gas into a catalyst layer.

The reaction temperature may be from about 250° C. to about 500° C., and preferably from about 300° C. to about 400° C. Although not outside the scope of the present invention, when it is lower than about 250° C., the reaction speed may be insufficient and the selectivity to ε-caprolactam tends to be lowered. Also again while not outside the scope of the present invention, when the temperature is over about 500° C., much cyclohexanone oxime may be thermally decomposed and the selectivity to ε-caprolactam also tends to be lowered.

The reaction temperature maybe controlled with a heat exchanger. Alternatively, the temperature may be controlled by mixing a gas that is inert to the reaction with a carrier gas (such as non-oxidizing gas) utilized in the reaction, or by spraying the raw material into the reactor to evaporate the raw material.

The reaction pressure may be any suitable pressure, and is preferably from atmospheric pressure to reduced pressure. The reaction pressure may be from about 5 kPa to 0.2 MPa, and preferably from about 5 kPa to 0.1 MPa.

The space velocity (WHSV) of the raw material, i.e. cyclohexanone oxime, may be from about 0.1 $h^{-1}$ to about 20 $h^{-1}$ in terms of WHSV (which means that the feeding speed of cyclohexanone oxime may be about 0.1 g/hr to about 20 g/hr per 1 g of the catalyst), and is preferably in the range of from about 0.2 $h^{-1}$ to about 10 $h^{-1}$.

In the rearrangement reaction of cyclohexanone oxime, it is preferred to use a lower alcohol having 1 to 8 carbon atoms, and more preferably a lower alcohol having 1 to 6 carbon atoms, with cyclohexanone oxime in the reaction. When the lower alcohol is used in the reaction, the selectivity to ε-caprolactam and catalyst life may be improved.

Examples of the lower alcohol include methanol, ethanol, n-propanol, isopropanol, n-butanol, sec-butanol, isobutanol, n-amyl alcohol, n-hexanol and the like. These lower alcohols may be used singly or in the combination of two or more of them. Preferably, the lower alcohol is methanol and/or ethanol. When a lower alcohol is used, the amount of the alcohol to be used may be from about 0.1 to 20 parts by weight, and preferably from about 0.2 to 10 parts by weight based on one part by weight of cyclohexanone oxime.

Separation of ε-caprolactam from the reaction mixture and purification thereof may be conducted by any suitable known method. For example, ε-caprolactam may be efficiently obtained by condensing the reaction mixture gas while cooling, and then, purifying ε-caprolactam in the mixture by extraction, distillation, crystallization or the like.

In either fixed-bed-type or fluidized-bed-type gas phase catalytic reaction, deposits (such as carbonaceous components, i.e., so-called coke, or precursor thereof) may be generated on the surface of the catalyst, when the reaction is continued for seven hours or more. These deposits result in a lower yield of the ε-caprolactam. In the present invention, the step for regenerating catalyst is conducted by treating the catalyst with a non-oxidizing gas at a temperature of from about 100° C. to about 600° C., for example, after the reaction step is conducted at a reaction temperature of from about 250 to about 500° C. for seven hours or more. By such a non-oxidizing gas treatment, deposits may be removed from the catalyst.

The regeneration of the catalyst using a non-oxidizing gas in the present invention usually does not release heat by oxidation of the deposits on the catalyst, which advantageously results in no adverse effect on the catalyst. Examples of non-oxidizing gas include inorganic gases, e.g. nitrogen and argon, and methane, and a mixture of two or more of them.

When the reaction is conducted in a fixed-bed- type reactor, the regeneration step may be carried out by a method in which a non-oxidizing gas is passed into the reactor to regenerate the catalyst after the supply of cyclohexanone oxime to the reactor is stopped. On the other hand, when the reaction is conducted in a fluidized-bed-type reactor, the rearrangement step may be carried out by inner circulation of the catalyst, i.e., by allowing the zeolite or non-zeolitic material to circulate between a reaction zone and a regeneration zone in a single vessel, or by outer circulation of the catalyst, i.e., by conducting the reaction step and the regeneration step respectively in a reaction vessel and in a regeneration vessel, and circulating the zeolite or non-zeolitic material between these vessels.

As described above, when using the fixed-bed-type reactor, the reaction may be stopped for the regeneration step, which may reduce productivity. On the other hand, the fluidized-bed-type reactor may provide a productivity higher than that with the fixed-bed-type reactor, by allowing the catalyst to continuously or discontinuously circulate between a reaction zone/vessel for the reaction step and a regeneration zone/vessel for the regeneration step.

A reactor, which is used in the method of the present invention with an inner circulation system, may comprise a reaction zone for converting cyclohexanone oxime into $\epsilon$-caprolactam in the presence of the catalyst (such as a zeolite or non-zeolitic material); a regeneration zone for treating the catalyst; and a means for conducting an inner circulation of the catalyst between these zones. In this reactor, it is preferred that the reaction zone and the regeneration zone are provided at an upper part and at a lower part of the reactor, respectively, so that a regenerated catalyst may be carried to the upper reaction part by a carrier gas.

The regeneration temperature should be a temperature sufficient to accelerate the removal of the deposits on the catalyst surface. The regeneration temperature may be from about 100° C. to about 600° C., and preferably is from about 100° C. to about 500° C.

In the present invention, deposits on the catalyst may be removed from the surface of the catalyst by a non-oxidizing gas. Further, a non-oxidizing gas may be employed as a carrier gas in the reaction step, which means that the reaction and regeneration may be conducted in a single vessel. This is because the reaction may also be conducted under a non-oxidizing gas atmosphere. In the present invention, the reaction and the non-oxidizing gas regeneration may be both conducted in the single vessel and are not always rigorously separated from each other. In this case, a mechanical open-and-shut device (such as a rotary valve) for separating the reaction and regeneration step from each other is not needed and, therefore, wear of the catalyst caused by the open-and-shut device may be advantageously decreased.

Figure 1:
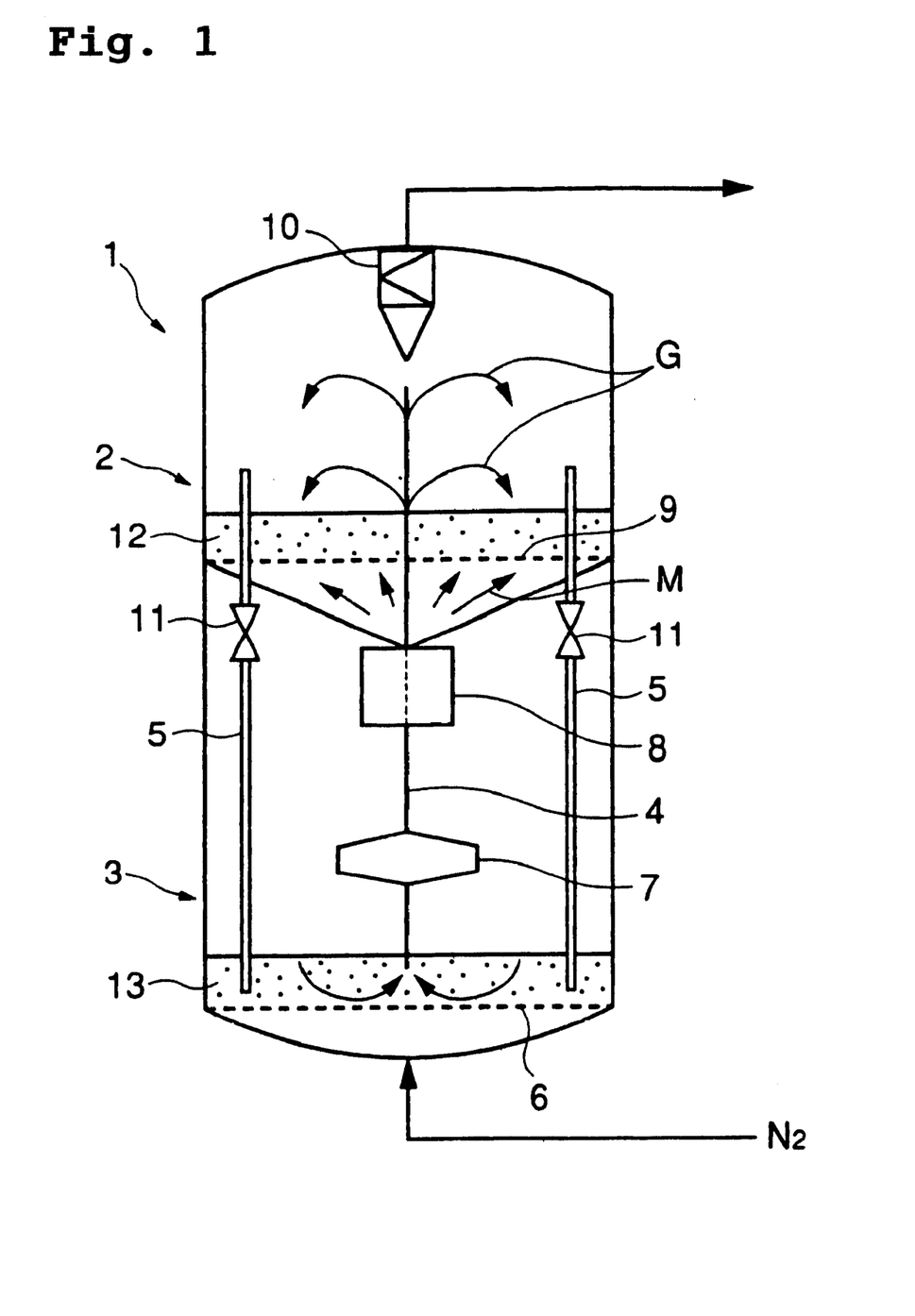
FIG. 1 is a schematic diagram of a reactor utilized in an embodiment of the present invention.

As described above, in the present invention, the reaction step and regeneration step may be conducted continuously in a single vessel in a fluidized-bed-type reactor by allowing the catalyst to circulate between a reaction zone and a regeneration zone. FIG. 1 illustrates one example of such a fluidized-bed-type reactor, which should not be construed as a limitation upon the scope of the present invention. As shown in FIG. 1, reactor 1 has reaction zone 2 and regeneration zone 3 in a single vessel.

Figure 2A:
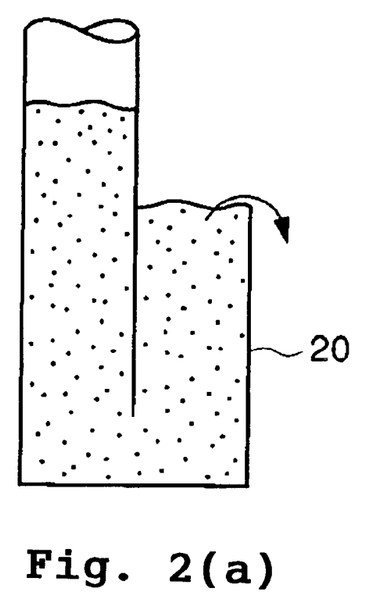
Figure 2B:
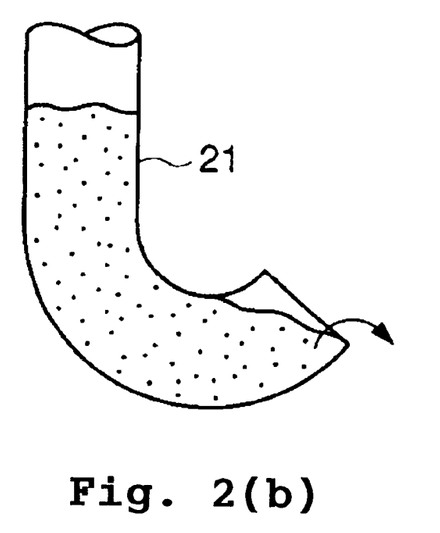
Figure 2C:
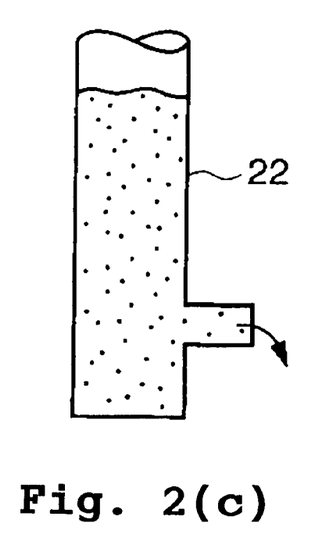

Reaction zone 2 placed in the upper part of the reactor is separate from the lower part of the reactor. Reaction zone 2 is connected with regeneration zone 3 by catalyst lift 4 having a gas-lift or the like and by a set of standpipes 5,5 or the like having U-valve 20, J-valve 21 or L-valve 22 (which are shown in FIG. 2 (a), (b) and (c), respectively) at the bottom thereof and positioned in regeneration zone 3. Alternatively, other mechanical or non-mechanical standard standpipe system (such as sluicing device) or the like may be used for standpipe 5. The set of standpipes 5,5 or the like may cope with the pressure difference between upper and lower zone of the reactor.

Catalyst lift 4 comprises a pipe, through which a catalyst in the form of powder or granule is conveyed from regeneration zone 3 to reaction zone 2. (The direction of the catalyst flow is shown with arrow "G"). A nitrogen gas for circulation of the catalyst is exhausted from the reactor through cyclone 10 which removes the catalyst having a prescribed particle size from the gas flow.

The flow of the catalyst through the catalyst lift 4 is conducted with a device which works similar to an airlift using a nitrogen gas as a carrier. The upward injection of the carrier gas from pressure chamber 7 positioned under the transferring lift (i.e., catalyst lift 4) results in suctioning and transferring the catalyst. When the catalyst in regeneration zone 3 is in a fluidized state, only small suction power is needed for transferring the catalyst. In that case, the amount of the carrier gas can be reduced and, therefore, the operation of the reactor may be conducted economically.

The set of standpipes 5,5 is placed so as to be partially located in reaction zone 2. The height of the upper openings of standpipes 5,5 may be determined depending on the amount of catalyst in reaction zone 2. When the amount of catalyst supplied from catalyst lift 4 is increased, the catalyst flows through standpipes 5,5 into regeneration zone 3. The residence time of the catalyst in regeneration zone 3 may be controlled with the amount of the catalyst flowing through catalyst lift 4. Standpipes 5,5 have valves 11,11 for controlling the amount of flow of the catalyst. Standpipes 5,5 by having valve 20, 21, 22 or the like at the bottom thereof provide a convenient way to collect catalyst and thereby stop or block the gas flow from reaction zone 2 into regeneration zone 3 and also stop or block the gas flow from regeneration zone 3 to reaction zone 2.

Regeneration zone 3 has bottom 6 (i.e., a gas distributor) of mesh or the like, and a non-oxidizing gas is introduced from below bottom 6. The catalyst in regeneration zone 3 is regenerated by being treated with the non-oxidizing gas.

Under the reaction zone 2, are placed supply tool 8 (e.g. pipe) and gas distributor 9. Supply tool 8 supplies the vaporized cyclohexanone oxime used as a material and a nitrogen gas used as a carrier (and the above-mentioned lower alcohol, if necessary.) Gas distributor 9 divides the reactor into two zones. of reaction zone 2 and regeneration zone 3. The gas phase catalytic reaction is carried out when the raw material and the like (which are supplied from supply tool 8 to reactor 1) pass through reaction zone 2. (The flow direction of the raw material and the like is shown by arrow "M".) The produced $\epsilon$-caprolactam is taken out from an upper part of reactor through cyclone 10. The catalyst deteriorating during the reaction flows through standpipes 5,5 into regeneration zone 3, so as to be regenerated in the atmosphere of the non-oxidizing gas (such as nitrogen or the like) in regeneration zone 3.

In reactor 1, the reaction step and regeneration step are conducted in a single vessel by allowing the catalyst (such as zeolite or non-zeolitic material) to circulate between reaction zone 2 and regeneration zone 3, and no mechanical open-and-shut device (such as a valve) is placed between zones 2 and 3. Therefore, the wear of the catalyst during circulation is reduced enormously, thereby prolonging lifetime of the catalyst and providing ease of operation and control of the reactor.

The reaction temperature in reaction zone 2 and the regeneration temperature in regeneration zone 3 may be controlled at the temperature of from about 250° C. to about 500° C. and at the temperature of from about 100° C. to about 600° C., respectively. The temperatures of zones 2 and 3 may be controlled by, for example, introducing water or steam for cooling or heating into coils installed in the zones.

Onto the catalyst used in the reaction, are adhered deposits that are mainly tar-like components having high boiling points and originated from the raw material or the reaction product. Deposits on the catalyst are removed by the treatment with the non-oxidizing gas to regenerate active sites on the catalyst.

In a continuous or repeated reaction, a small amount of deposits remaining after the non-oxidizing gas treatment may gradually accumulate on the surface of the catalyst and may cause deactivation of the catalyst. In the present invention, the catalyst treated with the non-oxidizing gas may be additionally treated with an oxygen-containing gas. In such a method that comprises the steps of removing almost deposits on the catalyst by treating the catalyst with non-oxidizing gas and then removing the remaining deposits by treating the catalyst with the oxygen-containing gas, the heat release by oxidation of the deposits is small and the amount of water generated due to the oxidation may also be small. This is because almost all deposits are removed from the catalyst in the non-oxidizing gas treatment and only a small amount of deposits is oxidized in the oxygen-containing gas treatment.

The oxygen-containing gas treatment may be conducted using a reactor or the like other than the reactor utilized for the reaction step and/or the non-oxidizing gas treatment. The capacity of the reactor for the oxygen-containing gas treatment and flow rate of the catalyst in the oxygen-containing gas treatment may be smaller than those in the reaction step and/or in the non-oxidizing gas treatment.

Figure 3:
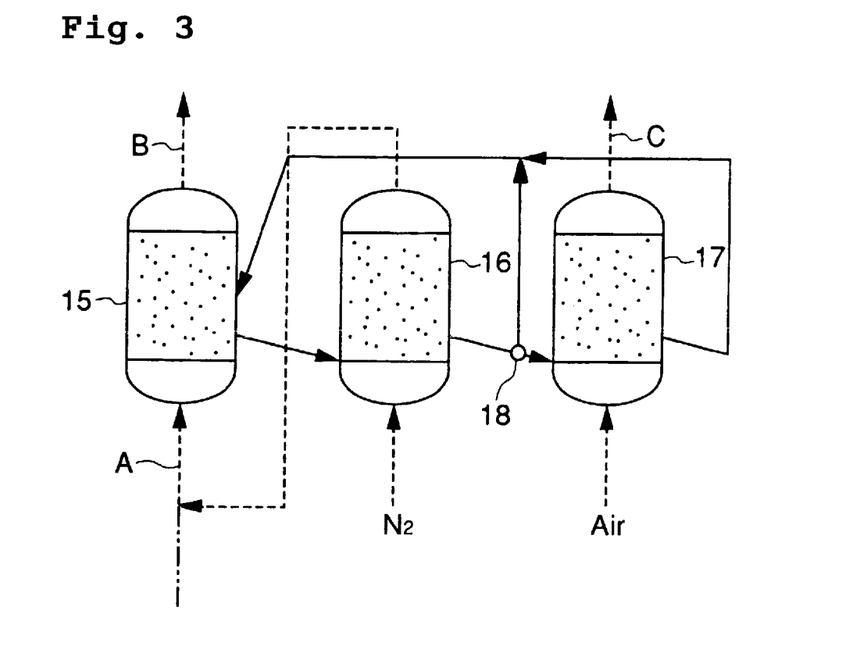
FIG. 3 is a schematic diagram of an operation system utilized in an embodiment of the present invention.

FIG. 3 illustrates one example of an operation system utilized for the two-stage regeneration (by the non-oxidizing gas treatment and the oxygen-containing gas treatment), which should not be construed as a limitation upon the scope of the present invention. As shown in FIG. 3, the system comprises fluidized-bed-type reaction column 15, fluidized-bed-type (or flow-type) first regeneration column 16 and fluidized-bed-type (or flow-type) second regeneration column 17. A prescribed amount of catalyst is packed into reaction column 15. From the bottom of the column 15, cyclohexanone oxime used as a raw material and a nitrogen gas used as a carrier (and the above-mentioned lower alcohol, if necessary) are introduced into reaction column 15, in which the gas phase catalytic reaction is conducted. (The direction of the flow of the raw material and the like is shown with arrow "A".) The ε-caprolactam produced therein is continuously taken out of the upper part of reaction column 15. (The direction of the flow of the ε-caprolactam is shown with arrow "B".)

The catalyst present in reaction column 15 which has an activity lower than that of the catalyst before the reaction is taken out of reaction column 15 and is then fed to first regeneration column 16. A non-oxidizing gas (such as a nitrogen gas) is introduced into first regeneration column 16 from the bottom of the column to conduct a first regeneration treatment of the catalyst therein. The temperature of the first regeneration treatment may be from about 100° C. to about 600° C., and preferably from about 150° C. to about 500° C. The residence time of the first regeneration treatment may be from about 0.5 to about 50 hours.

The catalyst thus treated with the non-oxidizing gas is then taken out from first regeneration column 16 and is sent to second regeneration column 17. The non-oxidizing gas in first regeneration column 16 is taken out of the upper part of the column and is sent to reaction column 15, as shown by the arrow in FIG. 3. In second regeneration column 17, the second regeneration step of the catalyst is conducted using an oxygen-containing gas (such as air). The temperature of the second regeneration treatment may be from about 300° C. to about 600° C., and preferably from about 300° C. to about 550° C. The residence time of the second regeneration treatment may be from about 1 to about 100 hours. The exhaust gas is discharged from the upper part of second regeneration column 17. (The flow direction of the exhaust gas is shown with arrow "C".) The catalyst regenerated in second regeneration column 17 is returned to reaction column 15. As described above, in the operation system in FIG. 3, the reaction step, the first regeneration step and the second regeneration step are continuously carried out by allowing the catalyst to circulate in reaction column 15, first regeneration column 16 and second regeneration column 17 in turn.

The oxygen-containing gas treatment of the catalyst shown in FIG. 3, namely second regeneration column 17, may be omitted. In that case, the catalyst treated with non-oxidizing gas in first regeneration column 16 is sent to reaction column 15. Three-way valve 18 is installed to switch the flow of the catalyst sent out of the first regeneration column 16.

EXAMPLES

The present invention is illustrated by the following Examples, which are not intended to limit the scope of the invention in any way.

In Examples and Comparative Example, conversion of cyclohexanone oxime and selectivity to ε-caprolactam were calculated using the below equations:

Conversion of cyclohexanone oxime (%)=

$[(X-Y)/X] \times 100$ Selectivity to ε-caprolactam $(\%)=[Z/(X-Y)] \times 100$ wherein X is a molar amount of supplied cyclohexanone oxime, Y is a molar amount of unreacted cyclohexanone oxime and Z is a molar amount of produced ε-caprolactam.

Reference Example
Preparation of [B]-MFI Zeolite Catalyst
[B]-MFI zeolite catalyst is prepared by a hydrothermal reaction as follows:

Boric acid (12.2 g) was mixed with an aqueous hexamethylenediamine solution (800 g, containing 12.2 g of hexamethylenediamine) and was completely dissolved therein. Into the solution, was added 64 g of $SiO_2$ (Aerosil). Within the next 10 min., the resulting mixture was put in an autoclave. The mixture was maintained in the autoclave over 14 days at 170° C. under autogeneous pressure, while stirring at a stirring rate of 50 rpm or less, to obtain crystals. After cooling, the crystals were filtered out and were washed with deionized water. The obtained white powder was dried at 110° C. and was calcined in the presence of air at 550° C. (total time of 12 hours for the drying and calcinations.) Due to the alkaline free synthesis, an ion exchange (to transform the Na-form of the zeolite into the catalytically active H-form) was not necessary and, therefore, was not carried out.

The powder was kneaded with water and a peptizing agent and then was extrudated to form strings with a diameter of 2 mm. The obtained extrudates were dried and calcined in the same manner as described above, and then were crushed and sieved to obtain a catalyst having a particle size of from 1 mm to 1.6 mm for a fixed-bed-type reactor and a catalyst having a particle size of from 80 μm to 200 μm for a fluidized-bed-type reactor.

Example 1

Using a fluidized-bed-type reactor charged with 25 g of [B]-MF1 catalyst prepared as described above, a gas phase Beckmann rearrangement reaction was conducted under the relatively severe conditions described below in order to illustrate the advantages of the present invention.

Specifically, a mixture of cyclohexanone oxime and ethanol (1:9 in ratio by weight) was vaporized and supplied to the reactor while using nitrogen (that is a non-oxidizing gas) as a carrier gas, to conduct a gas phase Beckmann rearrangement reaction at 400° C. under 0.1 MPa. The supplying rate of the cyclohexanone oxime was 1 g/hour, and that of the nitrogen gas was 26 L/hour.

The above reaction was conducted over 12 days, intermittently. That is, the reaction was conducted in daytime, whereas in nighttime the reaction was stopped by lowering the temperature to 120° C. and introducing a nitrogen gas into the reactor in place of the mixture of cyclohexanone oxime at a flow rate as low as possible so as to regenerate the catalyst.

The resulting reaction mixture was analyzed over time utilizing gas chromatography using methyl undecanate as an internal standard, to determine the conversion of cyclohexanone oxime and selectivity to $\epsilon$-caprolactam. The conversion and selectivity as a function of time are shown in FIG. 4.

Figure 4:
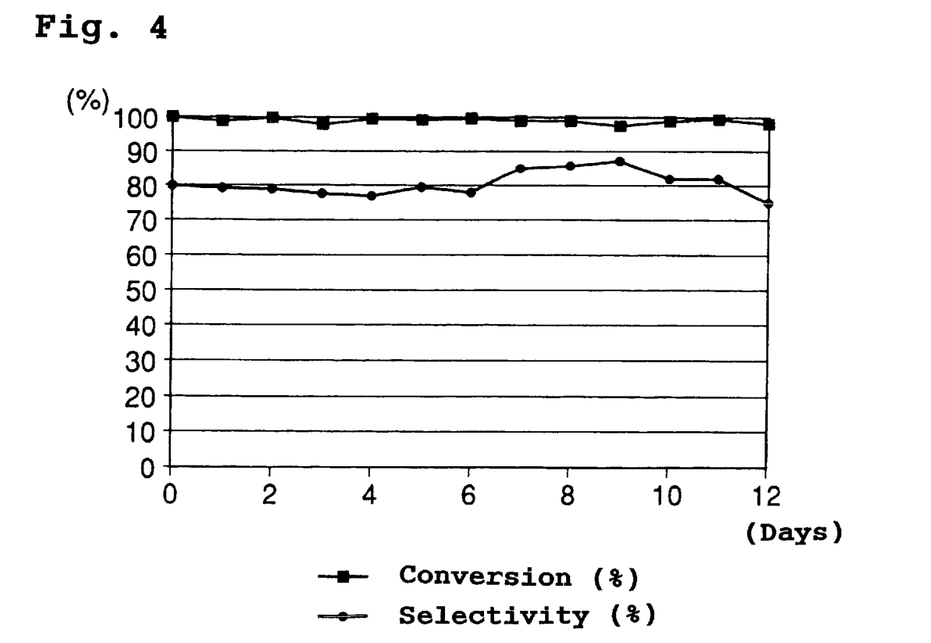
FIG. 4 is a chart of variations in conversion and selectivity as a function of time elapsed for in Example 1.

FIG. 4 shows that the conversion and selectivity were substantially maintained over 12 days, which means that activity of the catalyst was substantially maintained due to an effective regeneration of the catalyst with the nitrogen gas in accordance with the present invention.

Example 2

A gas phase Beckmann rearrangement reaction was conducted over two days under relatively severe conditions such that 180 g of a mixture of cyclohexanone oxime and ethanol (1:9 in ratio by weight) was used in the presence of about 20 g of the catalyst, so that coke uniformly generated on the surface of a [B]-MFI catalyst.

Figure 5:
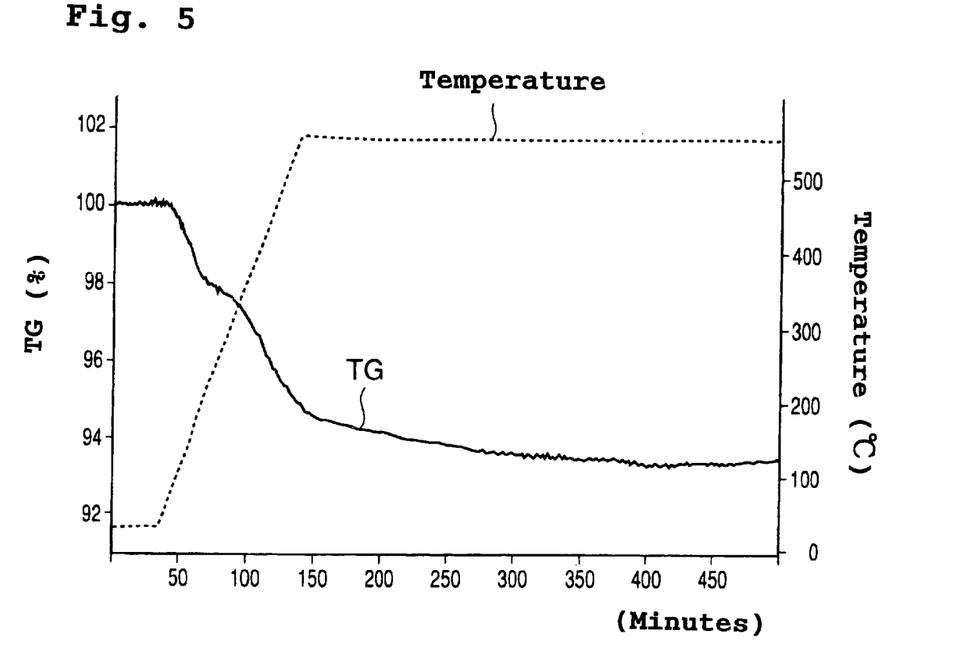
FIG. 5 is a thermogravimetry (TG) curve of the catalyst during the regeneration treatment with nitrogen conducted in Example 2.

The resulting catalyst was treated with a nitrogen gas. During the treatment, the weight loss of the catalyst in terms of thermogravimetry (TG) was measured over time. The results are shown in FIG. 5. In FIG. 5, the weight of the catalyst was reduced over time, showing that the coke which had been generated on the catalyst was removed from the catalyst by the nitrogen treatment and the catalyst was regenerated.

Figure 6:
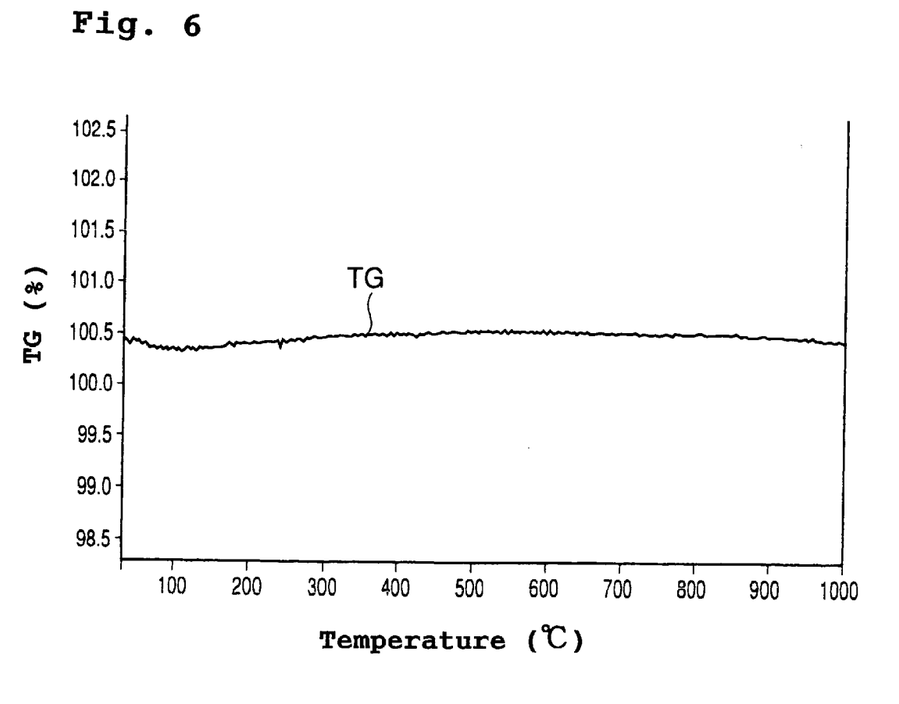
FIG. 6 is a thermogravimetry (TG) curve of the catalyst during the regeneration treatment with air conducted in Example 2.

Subsequently, the catalyst regenerated with nitrogen was treated with air. During the treatment, the weight loss of the catalyst in terms of thermogravimetry (TG) was measured over time. The results are shown in FIG. 6. In FIG. 6, the weight of the catalyst substantially did not change. It seems that in this case, almost all of the coke had been removed from the catalyst during the first treatment with nitrogen, not with the second treatment with air.

Example 3

0.375 g of a high silica MFI catalyst was packed into a fixed-bed-type reactor having an inner diameter of 10 mm. A mixture of cyclohexanone oxime and methanol (1:1.8 in ratio by weight) was vaporized and supplied to the reactor while using a nitrogen gas as a carrier, to conduct a gas phase Beckmann rearrangement reaction at 380° C. under 0.1 MPa with a space velocity (WHSV) of cyclohexanone oxime of 8 h$^{-1}$. The reaction was continued for 20 hours, and the resulting reaction mixture was analyzed over time utilizing gas chromatography. The results (i.e., conversion of cyclohexanone oxime and selectivity to $\epsilon$-caprolactam) are shown in the below Table 1 as the results obtained before regeneration of the catalyst.

Subsequently, the supply of the mixture of cyclohexanone oxime was stopped, and the temperature of the catalyst bed was adjusted to 410° C. while supplying a nitrogen gas. The regeneration treatment of the catalyst was conducted for five hours at 410° C. while supplying the nitrogen gas at a rate of 5.0 L/h.

Then, again the gas phase Beckmann rearrangement reaction of cyclohexanone oxime was conducted for 20 hours in the same manner as described above using the catalyst obtained after the regeneration treatment. The resulting reaction mixture was analyzed over time utilizing gas chromatography. The results (i.e., conversion of cyclohexanone oxime and selectivity to $\epsilon$-caprolactam) are shown in Table 1 as the results obtained after regeneration of the catalyst.

Example 4

The gas phase Beckmann rearrangement reaction of cyclohexanone oxime and the regeneration treatment of the catalyst with nitrogen were conducted in the same manner as in Example 3, except that the catalyst regenerated with nitrogen was treated with air by supplying air thereto at a rate of 5.0 L/h before being utilized in the second reaction. The resulting reaction mixtures (obtained in the first reaction and the second reaction) were respectively analyzed over time utilizing gas chromatography. The results (i.e., conversion of cyclohexanone oxime and selectivity to $\epsilon$-caprolactam) are shown in Table 1.

Comparative Example

The gas phase Beckmann rearrangement reaction of cyclohexanone oxime was conducted in the same manner as in Example 3 and was continued for 60 hours. The resulting reaction mixture was analyzed over time utilizing gas chromatography. The results (i.e., conversion of cyclohexanone oxime and selectivity to $\epsilon$-caprolactam) are shown in Table 1. Conversion was reduced over time, since the catalyst was not treated with nitrogen.

TABLE 1

|  | | First Reaction (*1) | | Second Reaction (*2) | |
|---|---|---|---|---|---|
|  | Reaction Time (hr) | Conversion (%) | Selectivity (%) | Conversion (%) | Selectivity (%) |
| Example 3 | 0 | 100 | 96.2 | 99.7 | 96.8 |
|  | 5 | 100 | 97.1 | 99.5 | 96.8 |
|  | 13 | 99.8 | 97.6 | 99.0 | 96.5 |
|  | 20 | 99.7 | 97.0 | 98.5 | 96.6 |
| Example 4 | 0 | 100 | 95.7 | 99.6 | 96.3 |
|  | 5 | 99.9 | 96.7 | 99.2 | 96.8 |
|  | 13 | 99.6 | 97.8 | 98.8 | 97.7 |
|  | 20 | 99.3 | 97.0 | 98.0 | 97.1 |
| Comparative Example | 0 | 100 | 96.6 |  |  |
|  | 5 | 99.8 | 97.8 |  |  |
|  | 20 | 98.8 | 97.3 |  |  |
|  | 40 | 95.9 | 97.1 |  |  |
|  | 60 | 91.7 | 96.9 |  |  |

(*1) Reaction conducted before the regeneration treatment of the catalyst
(*2) Reaction conducted after the regeneration treatment of the catalyst The invention being thus described, it will be apparent that the same may be varied in many ways. Such variations are to be regarded as within the spirit and scope of the invention, and all such modifications as would be apparent to one skilled in the art are intended to be within the scope of the following claims.

What is claimed is:

1. A method for producing $\epsilon$-caprolactam from cyclohexanone oxime, the method comprising a reaction step for converting the cyclohexanone oxime into ε-caprolactam in the presence of a catalyst, the reaction being conducted under gas phase reaction conditions; and a regeneration step for treating the catalyst with a non-oxidizing gas at a temperature of from about 100° C. to about 600° C., and an additional regeneration step for treating the catalyst with an oxygen-containing gas at a temperature of from about 300° C. to about 600° C., after the regeneration step with the non-oxidizing gas.

2. The method according to claim 1, wherein the reaction step and the regeneration step are conducted in a single vessel having a reaction zone and a regeneration zone, and the catalyst is circulated between the reaction zone and the regeneration zone.

3. The method according to claim 1, wherein the reaction step and the regeneration step are conducted in a reaction vessel and a regeneration vessel, respectively, and the catalyst is circulated between the reaction vessel and regeneration vessel.

4. The method according to claim 1, wherein the catalyst is, in turn, continuously or discontinuously circulated in a reaction vessel or zone, in a regeneration vessel or zone for the regeneration step with the non-oxidizing gas, and in an additional regeneration vessel for the additional regeneration step with an oxygen-containing gas.

5. The method according to claim 1, wherein the catalyst is a zeolite catalyst.

6. The method according to claim 1, wherein the reaction step for converting the cyclohexane oxime, into ε-caprolactam is conducted in the presence of a lower alcohol having 1 to 8 carbon atoms.

7. The method according to claim 5, wherein the catalyst is a pentasil zeolite catalyst.

8. The method according to claim 1, wherein the catalyst is selected from the group consisting of an aluminophosphate and a siliciumaluminophosphate.

* * * * *